US005739210A

United States Patent [19]

Scranton et al.

[11] Patent Number: 5,739,210
[45] Date of Patent: Apr. 14, 1998

[54] POLYMERS COMPRISING REVERSIBLE HYDROPHOBIC FUNCTIONALITIES

[75] Inventors: Alec B. Scranton; Arvind M. Mathur, both of East Lansing; John Klier, Midland, all of Mich.

[73] Assignee: Michigan State University, East Lansing, Mich.

[21] Appl. No.: 695,237

[22] Filed: Aug. 8, 1996

Related U.S. Application Data

[60] Provisional application No. 60/006,211, Nov. 3, 1995.
[51] Int. Cl.$^6$ ........................................... C08F 8/14
[52] U.S. Cl. .................... 525/279; 525/283; 525/296; 525/330.1; 525/384
[58] Field of Search ......................... 525/330.1, 279, 525/283, 296

[56] References Cited

U.S. PATENT DOCUMENTS

| | | | |
|---|---|---|---|
| 4,771,105 | 9/1988 | Shirai et al. | 525/330.1 |
| 5,336,728 | 8/1994 | Humphries et al. | 525/330.1 |
| 5,422,394 | 6/1995 | Taylor et al. | 525/330.4 |

*Primary Examiner*—Bernard Lipman
*Attorney, Agent, or Firm*—Price, Heneveld, Cooper, Dewitt & Litton

[57] ABSTRACT

Polymers comprising reversible hydrophobic functionalities are disclosed. The preferred embodiment polymers comprise Lewis acid segments and Lewis base segments. The polymer segments are, by themselves, hydrophilic and will either swell or dissolve in water. When the segments are incorporated into a polymer according to the present invention, the segments form water-insoluble or hydrophobic complexes. Upon changes in pH, temperature or solvent type, these complexes may dissociate, giving large transitions in polymer viscosity, emulsification ability, mechanical strength or transport properties. These polymers are useful as reversible emulsifiers which form stable emulsions at acidic pH and unstable emulsions at basic pH, as water-borne thickeners having low viscosity at low pH and high viscosity at high pH, as superabsorbing resins, or as coatings for pharmaceutical or agricultural agents.

1 Claim, 2 Drawing Sheets

POLYMERS COMPRISING REVERSIBLE HYDROPHOBIC FUNCTIONALITIES

This application claims benefit of U.S. Provisional Application No. 60/006,211, filed Nov. 3, 1995.

FIELD OF THE INVENTION

The present invention relates to a unique class of polymers that can selectively be rendered hydrophobic, hydrophilic, or amphipathic. The ability to selectively alter the solvent affinity characteristics of the polymers is remarkable and provides a new class of materials and related methods of use, particularly for reversible emulsifiers, thickeners, superabsorbent materials, and pharmaceutical coatings.

BACKGROUND OF THE INVENTION

Polymeric emulsifiers, thickeners and superabsorbers are well known. Polymeric emulsifiers have been used to stabilize oil droplets in water for a variety of applications including, but not limited to, aqueous cleaning operations, suspension polymerization, food applications, cosmetics, pharmacy, agriculture and bitumen processing. The emulsifiers generally contain both hydrophilic and hydrophobic groups, giving the polymer an "amphipathic" character. Examples of such polymeric emulsifiers and their properties are described in standard texts such as Irja Pirma, *Polymeric Surfactants*, Marcel Dekker, 1992. This text summarizes an extensive body of literature regarding hydrophilic/ hydrophobic diblock, triblock, graft and random copolymers. Specific examples of polymeric emulsifiers are provided in Great Britain Patent GB 2,115,002A to Baker (1983), which discloses block or graft copolymers of hydrophobic monomers with hydrophilic monomers. U.S. Pat. No. 5,021,526 to Ball, describes random terpolymer emulsifiers made from water-soluble vinyl monomers, water-insoluble vinyl monomers containing 12 to 30 carbon atoms, and polymerizable acid monomers. In addition, hydrophobically functionalized crosslinked polyacrylic acid may be used as polymeric emulsifiers, as reported by R. Y. Lochhead ACS Symposium Series, Vol. 462, 101 (1991). In all of these examples, the molecular structure of the emulsifier contains both hydrophobic and hydrophilic groups to achieve an amphipathic nature. In general, the hydrophilic groups may be anionic, cationic or nonionic in nature. Multiblock copolymer architectures have not been used in practice as emulsifiers, although recent theoretical work suggests that multiblock copolymers would be more efficient than standard di- or triblock systems, J. Noolandi, *Makrotool. Chem. Theory Simul.*, 1(5) 295–8, (1992). Furthermore, although there has been very limited discussion of polymeric emulsifiers which allow the emulsion to be reversibly formed and broken, as discussed in Great Britain Patent GB 2,006,744A to Sonnergard (1979), no such emulsifiers which are truly effective have yet been obtained.

Alkali swellable or alkali soluble thickeners (AST's) have found wide application for thickening paint, coating, textile, consumer product, and adhesive formulations. In general, these thickeners exhibit low viscosity under acidic conditions, and high viscosity under basic conditions making them easy to manufacture and blend into formulations while providing excellent thickening properties in the final formulation upon pH adjustment. As described in several reviews and monographs (G. D. Shay, *Advances in Chemistry*, 223, 457 (1989) and Toshio Murakami, R. H. Fernando, J. E. Glass, *Surface Coating International*, 76, 8 (1993)), these thickeners are typically produced by emulsion polymerizations of acrylic or methacrylic acid with a hydrophobic monomer such as ethyl acrylate. The acid groups may be positioned on the surface of the resulting beads by semi-batch or multi-stage addition of the hydrophilic monomer in the latter stages of an emulsion polymerization such as described in U.S. Pat. Nos. 5,266,646 and 5,451,641 to Eisenhart. Generally, such polymers contain more than 40 wt. % of the hydrophobic monomer. For example, Murakami et al., teach compositions containing 48–51 wt. % of the hydrophobic monomer, Toshio Murakami, R. H. Fernando, J. E. Glass, *Surface Coating International*, 76, 8 (1993). Rodriguez and Wolfe report systems containing 66 wt. % of the hydrophobic ethyl acrylate monomer and 33 wt % of the hydrophilic methylmethacrylate monomer, *Macromolecules*, 27, 6642 (1994). U.S. Pat. No. 4,351,754 to Duprey, teaches that at least 30% alkyl methacrylates with one to four carbon atoms must be used. U.S. Pat. No. 4,801,671 to Shay, teaches compositions with 15% to 50% carboxy monomer, 10% surfactant monomer, and the balance being a hydrophobic ethyl acrylate monomer. When utilizing high amounts of hydrophilic acidic monomer, it is often necessary to include crosslinking agents to maintain insolubility and high thickening efficiency, Toshio Murakami, R. H. Fernando, J. E. Glass, *Surface Coating International*, 76, 8 (1993).

Water-insolubility of the emulsifiers and thickeners described above is provided via hydrophobic comonomers or functional groups such as aliphatic esters of acrylic or methacrylic acid. Polymeric emulsifiers also contain hydrophobic comonomers to impart compatibility with the emulsified oil phase, while thickeners contain hydrophobic comonomers to provide water insolubility at acidic pH. These classes of materials have never previously been made by aqueous emulsion or suspension polymerization without hydrophobic comonomers or hydrophobic functional groups.

Superabsorbent polymers are used in applications which require high water absorbency, as described in many recent reviews, for example, L. Brannon-Peppas and R. S. Harland, *Absorbent Polymer Technology*, Elsevier, 1990; and F. L. Buchholz and N. A. Peppas, *Superabsorbent Polymers, Science and Technology*, ACS Symposium Series, vol. 573, 1993. As noted in these works, superabsorbent polymers are typically crosslinked water-soluble polymers or copolymers of monomers containing carboxylic acids. Upon contact with water, the polymers swell to imbibe the aqueous fluid. As a result of their hydrophilic character and resulting high degree of swelling, these materials cannot be made via suspension or emulsion polymerization in water, and are typically produced by bulk, solution, or inverse-suspension polymerization in organic solvents. Depending upon the end product, it would be desirable in some instances, to form superabsorbent polymers via suspension or emulsion polymerization techniques.

Polymers which are sensitive to pH have been widely used in pharmaceutical and agricultural controlled-release formulations, see for example, *Advances in Polymer Science*, Vol. 122 Springer Verlag Berlin Heidelberg, 1995. In particular, such polymers have been used as coatings, and in particular, as enteric coatings. Typically, copolymers of hydrophilic carboxy or amine functional monomers with hydrophobic water-insoluble monomers are described for such coatings. These materials provide water-insoluble coatings at one pH, thereby preventing drug diffusion and release. At a second pH, the coatings become water-permeable or water-soluble resulting in drug delivery. For example, medications are commonly coated with enteric coatings which are water-insoluble at the acidic pH of the stomach and water-soluble in the basic pH of the intestine.

In all of these applications, there is a need for reversible, rather than permanent, hydrophobic functionality. In the case of emulsifiers, reversible hydrophobicity would allow emulsions to be broken or formed at will for ease of cleanup, phase separation, and reuse. In the case of thickeners, reversible hydrophobicity would enable high thickening efficiency at a particular pH. In the case of superabsorbers, it is desirable for the material to be water-insoluble during manufacture to facilitate synthesis via aqueous suspension polymerization, while being completely hydrophilic in the end-use formulation. Reversible hydrophobicity would enable the superabsorbent material to be water-insoluble during manufacture and water-soluble in the final formulation and would thereby allow manufacture of such polymers via suspension or emulsion polymerization techniques. In the case of pharmaceutical coatings, hydrophobic comonomers are required only to provide water-insolubility at a particular pH and may actually be detrimental at the release pH. Thus, it would be desirable to provide a polymer having a temporary or reversible hydrophobic characteristic, particularly if that characteristic could be selectively activated or deactivated.

All of the foregoing objectives could be achieved by incorporating a reversible hydrophobic group into a polymer, which group may be converted to a hydrophilic group upon change in pH, temperature, solvent, or some other parameter.

SUMMARY OF INVENTION

The present invention provides a class of polymers comprising reversible hydrophobic functionalities. In a preferred embodiment, the polymers comprise about 1% to about 95% hydrophilic segments comprising Lewis base functional groups (B segments), and about 5% to about 99% hydrophilic segments comprising Lewis acid functional groups (A segments). By themselves, the A and B segments are water-soluble or water-swellable. When combined under appropriate conditions, the A and B segments are capable of forming water-insoluble complexes which can be reversibly broken or de-complexed via changes in pH, temperature or solvent polarity. This reversible complexation results in large changes in the polymer's solubility in water, and may be utilized to achieve large reversible changes in emulsion stability, solution or dispersion viscosity, particle size, permeability, equilibrium swelling, etc. This unique class of polymers finds particular application as emulsifiers, thickeners, superabsorbing materials and pharmaceutical coatings.

DETAILED DESCRIPTION OF THE PREFERRED EMBODIMENT

The present invention provides a class of polymers having the following formula:

where:
A= segment comprising Lewis acid functional group(s);
B= segment comprising Lewis base functional group(s);
C= optional hydrophilic segment;
D= optional hydrophobic segment;
Xa= moles of A;
Xb= moles of B;
Xc= moles of C; and
Xd= moles of D;

As used herein, the term "hydrophilic segment" is meant to encompass a single hydrophilic group containing moiety or unit, as well as two or more repeating units which contain a hydrophilic group. Likewise, the term "hydrophobic segment" is meant to encompass a single hydrophobic group containing moiety or unit, as well as two or more repeating units which contain a hydrophobic group.

The preferred embodiment polymers of the present invention are graft or block copolymers which comprise A and B polymer segments or sequences that, under certain conditions, can be characterized as containing Lewis acid and Lewis base monomer repeating units, respectively. As previously noted, the A and B segments by themselves, are water-soluble or water-swellable. That is, the A or B segments, if not incorporated into a polymer, are water-soluble and so readily dissolve in an aqueous environment. The term "water-swellable" as used herein, means that the A or B segments, if not incorporated into the polymers described herein, can absorb or imbibe water to a degree of at least 50% of the weight of the respective A or B segment. A segments comprise Lewis acid monomer repeating units. "Lewis acid monomer repeating units" as that term is used herein, refers to one or more monomers having electron deficient hydrogen atoms and which are not ionized. Examples of A segments which include Lewis acid monomer repeating units include, but are not limited to, acrylic acid, methacrylic acid, itaconic acid, maleic acid and vinyl phenol in their protonated states, among others. Most preferred examples of A segments include acrylic acid and methacrylic acid. It is contemplated that the A segments may comprise combinations of the aforementioned units, or comprise combinations of those units with other monomers or groups. For example, the A segment could comprise one or more repeating units of a copolymer of acrylic acid and methacrylic acid, either by itself or in combination with other monomers or groups.

As noted, B segments generally comprise "Lewis base monomer repeating units." That term as used herein, refers to units that are not ionic, yet have some basic character. Examples of B segments which include Lewis base monomers include, but are not limited to, ethylene oxide, ethylene glycol, vinyl pyrrolidone, acrylamide monomers, or other alkylene oxides such as propylene oxide and butylene oxide, among others. Most preferred examples of B segments include segments having ethylene glycol monomer repeating units such as oligo(ethylene glycol) monomethacrylate having a nominal Mn of the ethylene glycol repeat unit ranging from about 200 to about 1000; and behenyl poly (ethylene oxide) methacrylate having a nominal Mn of ethylene oxide chain of about 1100. As previously noted with regard to the A segments, it is also contemplated that the B segments may comprise combinations of the aforementioned units, or comprise combinations of those units with other monomers or groups.

The preferred embodiment polymers of the present invention comprise about 1% to about 95% (all percentages expressed herein are mole percentages except if noted otherwise) B segments, and about 5% to about 99% A segments. The preferred embodiment polymers further comprise A segments and B segments in particular ratios with respect to each other. The preferred molar ratio of A segments to B segments is from about 0.01:1 to about 100:1.

Segment C is a hydrophilic monomer. It is optional to include segment C in the polymers of the present invention. An example of segment C is 2-acrylamido-2-propane sulfonic acid. The amount of C segments in the preferred embodiment polymers ranges from about 0 to about 10% of the total A segments in the polymer. As previously noted with regard to the A and B segments, the C segment may also comprise more than one type of monomer.

Segment D is a hydrophobic monomer. The polymers of the present invention optionally contain segment D. Examples of segment D include, but are not limited to, lauryl methacrylate or lauryl acrylate. The amount of D segments in the preferred embodiment polymers ranges from about 0 to about 10% of the total A segments in the polymer. As previously noted in the discussion of the A and B segments, the D segment may also comprise more than one type of monomer.

The preferred embodiment polymers comprise a backbone formed primarily from hydrophilic A segments, and branches or grafts that are primarily hydrophilic B segments. The preferred embodiment polymers may further comprise minute amounts of optional segments C and D. As described in greater detail below, segments A and B form a stable hydrophobic complex under acidic conditions while the complex is broken under basic conditions resulting in a hydrophilic polymer.

It should be noted that repeating units such as acrylic acid or methacrylic acid can be transformed from their Lewis acid form (protonated) to a basic form (ionized, neutralized) by increasing aqueous phase pH, from acidic to basic. Thus, complexation between poly(acrylic acid) and poly(ethylene glycol) sequences is reversible and pH-sensitive, with acid-base complexes forming at acidic pH and breaking at basic pH. The resulting copolymers form intramolecular complexes under acidic conditions between the acrylic acid and ethylene glycol repeating units in water. If the Lewis acid and Lewis base monomer repeating units are present in a stoichiometric 1:1 molar ratio, then the polymer will precipitate in water.

The copolymers of this invention are generally prepared by polymerization in an aqueous medium under complex promoting conditions. The preferred embodiment polymers of the present invention can be prepared via free radical polymerization to produce block or graft polymers. Preferably, they are prepared via copolymerization of vinyl Lewis acid monomers with macromonomers containing a sequence of Lewis base monomers. For example, copolymers of the present invention can be formed by copolymerizing ethylenically unsaturated monocarboxylic acids with macromonomers comprising ethylenically unsaturated esters of a monocarboxylic acid, esterified with a poly (alkylene oxide), such as poly(ethylene oxide). The polymers of the present invention may also be synthesized by solution polymerization in alcohol/water mixtures or by emulsion polymerization in water under complex-promoting conditions. In particular, the Lewis acid monomers, e.g. acrylic or methacrylic acid, can be copolymerized with the Lewis base macromonomer poly(ethylene glycol monomethyl ether) methacrylate using hydrogen peroxide in a 1:1 ethanol: water mixture to form poly(acrylic acid) with poly(ethylene glycol) grafts. Alternatively, Lewis acid monomers can be polymerized in the presence of a Lewis base oligomer (such as polyethylene glycol with a molecular weight greater than 2,000 or a polyethylene glycol sequence which is part of a larger molecule) without the use of a macromonomer. In this case, the integrity of the polymer colloid is maintained primarily by intermolecular complexes (although some grafting of the acid monomer onto the polyethylene glycol can occur) without requiring the use of a macromonomer.

Complexing polymers of the present invention can be readily identified using a simple solubility or swelling test. If the parent polymers are independently water-soluble, or swell in water to a certain extent, while the copolymer is water-insoluble or swells to a significantly lower extent under otherwise identical conditions, then complexation is occurring. For example, poly(acrylic acid) and poly (ethylene glycol) are each water-soluble at acidic pH. However, the stoichiometric copolymer containing a 1:1 monomer repeating unit ratio of acrylic acid and poly (ethylene glycol methacrylate) is water-insoluble. Thus, complexation is occurring. If methacrylic acid is substituted for acrylic acid, the poly(methacrylic acid) is not water-soluble but has a very high water uptake (~90%) under acidic conditions. In contrast, the stoichiometric copolymer with poly(ethylene glycol methacrylate) has a very low water uptake (less than 25 wt %).

Figure 1A:
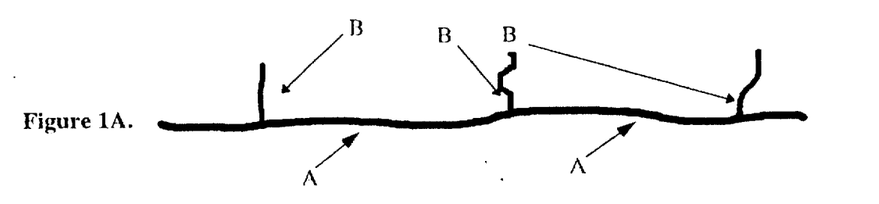
FIG. 1 illustrates the reversible configurations of the polymers of the present invention.
Figure 1B:
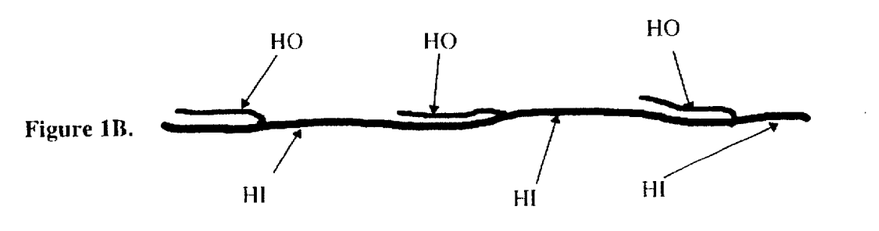

FIGS. 1A and 1B illustrate the reversible configurations of the polymers of the present invention. FIG. 1A illustrates a copolymer comprising a backbone of primarily A segments and a plurality of branching B segments disposed along the polymer backbone. In the uncomplexed state generally depicted in FIG. 1A, all portions of the polymer are hydrophilic and the polymer exhibits a particular set of properties or characteristics at that state. When in its complexed state as illustrated in FIG. 1B, the B segments complex with A segments along the polymer backbone. The resulting complexation causes previously hydrophilic portions of the polymer, i.e. B segments and those A segments that complex with the B segments, to become hydrophobic, designated as HO in FIG. 1B. Depending upon the ratio of B segments to A segments, and length or configurations of B segments, portions of the polymer may remain "exposed" when the polymer is in its complexed state. Such exposed regions are still hydrophilic and are designated in FIG. 1B as HI.

Figure 2:
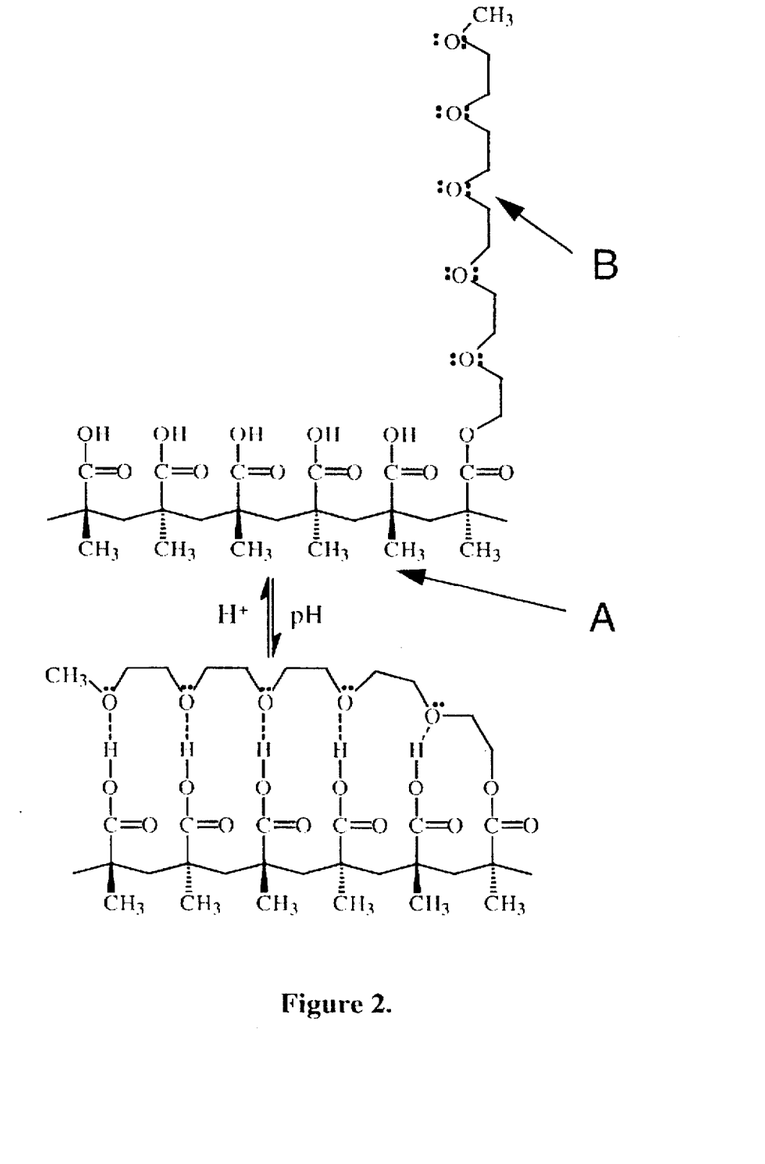
FIG. 2 illustrates in greater detail the reversible configurations and complexing arrangement of the present invention polymers.

FIG. 2 illustrates in greater detail the complexation occurring between A and B segments of a preferred embodiment polymer of the present invention. In this scheme, complexation occurs via hydrogen bonding along the respective segments at acidic conditions.

Nonstoichiometric complexing polymers of the present invention are useful as reversible emulsifiers. Under complex promoting conditions, the polymers assume an amphipathic structure, with hydrophilic (non-complexed) regions and water-insoluble hydrophobic regions, as illustrated in FIGS. 1A, 1B and 2. These materials are capable of forming highly stable emulsions of oil in water. When the complexes are broken, such as via a pH change, the polymers become completely hydrophilic and the emulsions break. This behavior may be particularly useful in industrial cleaning applications where an effective emulsifier is required in one stage of the process, while emulsion breakage and oil skimming is required in a subsequent stage. Thus, the polymers of the present invention comprise novel reversible hydrophobic groups and do not require an inherently hydrophobic group.

Nonstoichiometric polymers of the present invention are also useful as novel polymeric thickeners which can be produced or delivered as aqueous emulsions or aqueous dispersions. Under complex-promoting conditions, the water-insoluble complexed segments are stabilized by the water-soluble polymer not involved in the complex. As a result, these polymers can form colloidal dispersions with a highly compact structure and low viscosity. Upon neutralization, the complexes dissociate and the polymers become completely hydrophilic, giving the desired thickening behavior. Thus, the complex forming polymers provide a novel, convenient mechanism for synthesis and delivery of the polymers as low viscosity colloidal dispersions in water. Upon neutralization, the desired thickening action is achieved.

Stoichiometric complexes of the present invention are also useful as superabsorbing polymers. Under complex promoting conditions, the acidic and basic monomers may be polymerized in water using suspension or emulsion polymerization into polymer beads. Upon neutralization and drying, hydrophilic crosslinked superabsorbing polymers result. Thus, these polymers comprise novel superabsorbing resins which can be synthesized by suspension or emulsion polymerization in water, without the use of hazardous organic solvents, while avoiding homogeneous or bulk polymerization which can give rise to high viscosity and difficult handling.

It is contemplated that the techniques and polymers of the present invention will also enable production of copolymers of acrylic acid or methacrylic acid, and long chain polyethylene glycol via suspension polymerization in an aqueous environment. Conventional suspension polymerization of polyethylene glycol and acrylic acid or methyacrylic acid require each reactant macromolecule be hydrophilic. The intermediate reaction product is relatively hydrophobic, and so an organic solvent must be used to sustain the resulting dispersion. The present invention enables the formation of microparticles of the resulting polymeric product in an aqueous environment without the necessity of an organic solvent.

The polymers of the present invention are also useful as coatings for pharmaceutical or agricultural agents, and in particular as enteric coatings. Polymers comprising reversible hydrophobic groups provide a selective release function. The polymers can provide water-insoluble coatings at one pH or pH range, thereby preventing release of the active. At a second pH, the polymers can become water-permeable or water-soluble, thereby enabling release of the active. The polymers of the present invention do not require permanent hydrophobic groups to achieve water-insolubility at certain pH values, which groups may actually be detrimental at the release pH.

A wide array of applications are contemplated for the polymers of the present invention. Representative applications include, but are not limited to, dispersants, polymeric detergents, flocculating agents, suspending agents, rheological control or modifying agents, encapsulating agents, controlled-release formulations including topical medicaments, consumer product controlled-release or delivery agents, micelle enhanced ultrafiltration agents, and removable inks or coatings.

EXAMPLES

Example 1

This example illustrates solution polymerization synthesis of complexing graft copolymer emulsifiers and thickeners according to the present invention which contain reversible hydrophobic functionalities synthesized by the free radical polymerization of methacrylic acid (MAA) with the macromonomer methoxy poly(ethylene glycol-1000) monomethacrylate.

The copolymer of methacrylic acid and poly(ethylene glycol) methacrylate was synthesized using free radical polymerization in a 1:1 ethanol and water mixture as described in Table 1 set forth below. The ratio of methacrylic acid repeat unit to ethylene glycol (EG) repeat unit was varied as described below.

In a clean glass vial, methacrylic acid (from Aldrich) and methoxy oligo(ethylene glycol) methacrylate (MPEGMMA) 1000 (with an average of 22.7 EG repeat units per mole, from Polysciences), were weighed and to this mixture was added 8 grams of deionized water, 8 grams of 200 proof ethanol (to form a 50/50 EtOH/water mixture as solvent) and 0.12 ml of 30% hydrogen peroxide solution (as initiator). The contents of the vial were mixed until a clear solution was observed. The vial was then sealed and placed in a water bath maintained at 80° C. The reaction was allowed to proceed for about 60 hours after which the viscous polymeric solution was placed in an oven at 80° C. to dry for 2–3 days. The dried polymer was removed from the vial and ground to a fine powder. Table 1 shows the water solubility of the polymers in deionized water. About 0.5 wt. % of polymer was added to 100 ml of deionized water in a bottle and stirred until dissolution.

TABLE 1

Synthesis of PMAA-g-PEG1000 copolymers for different MAA:EG repeat unit ratios.

| Methacrylic acid to ethylene glycol repeat unit ratio (MAA:EG) | MAA added (grams) | MPEGMMA 1000 added (grams) | Water solubility |
|---|---|---|---|
| 10:1 | 3.822 | 0.210 | soluble |
| 15:1 | 3.859 | 0.148 | soluble |
| 20:1 | 3.9782 | 0.028 | soluble |
| 100:1 | 3.9861 | 0.022 | soluble |
| inf:1 (pure PMAA) | 4.0081 | — | soluble |

Example 2

This example illustrates solution polymerization synthesis of complexing graft copolymer emulsifiers and thickeners according to the present invention. The polymers comprised reversible hydrophobic functionalities synthesized by free radical polymerization of methacrylic acid with the macromonomer, methoxy poly(ethylene glycol-1000) monomethacrylate, and addition of relatively small quantities of hydrophilic or hydrophobic comonomers.

Complexing copolymers containing small quantities of non-complexing hydrophilic or hydrophobic comonomers were synthesized using the procedure of Example 1 except for the addition of either the hydrophilic comonomer 2-acrylamido-2-methylpropane sulphonate (AMPS) or the hydrophobic comonomer lauryl methacrylate (LM). The amount of these comonomers was about 5–10 mole % of the carboxylic acid.

Example 3

This example illustrates solution polymerization synthesis of complexing graft copolymer emulsifiers and thickeners of the invention comprising reversible hydrophobic functionalities synthesized by free radical polymerization of acrylic acid (AA) with macromonomers of methoxy oligo(ethylene glycol) monomethacrylate (MPEGMMA).

The copolymer of acrylic acid and poly(ethylene glycol) methacrylate was synthesized using free radical polymerization in a 1:1 ethanol and water mixture as described in Table 2 set forth below. Solutions containing 20% monomer (by weight) in varying molar ratios, 40% ethanol, 40% water, and 0.4% VAZO-52 initiator, were prepared as described below. VAZO-52 is a free radical initiator available from DuPont. The solutions were placed in sealed high pressure glass reactor vessels. These vessels were then placed in a water bath at 60° C. for 72 hours.

TABLE 2

Mole percent of monomers in copolymerizations.

| Sample ID | Mole % EG (in MPEGMMA feed) | Mole % AA (in AA feed) |
|---|---|---|
| 9501070-29-1 | 89.49 | 10.51 |
| 9501070-29-2 | 74.77 | 25.23 |
| 9501070-29-3 | 50.22 | 49.78 |
| 9501070-29-4 | 24.64 | 75.36 |
| 9501070-29-5 | 9.90 | 90.10 |
| 9501070-29-6 | 5.41 | 94.59 |

Example 4

This example illustrates the synthesis of complexing copolymer latex thickeners comprising reversible hydrophobic functionalities synthesized by aqueous free radical emulsion polymerizations.

Copolymers of acrylic acid (AA) or methacrylic acid (MAA) and methoxy oligo(ethylene glycol-1000) monomethacrylate (MPEGMMA) 1000 were synthesized using free radical emulsion polymerization in a water and alcohol mixture using the procedures described in Table 3 below and the following text.

The procedure for polymerization of either AA or MAA with MPEGMMA 1000 is the same and the only variable is the MAA to EG repeat mole ratio. Initially a 1000 ml reactor is charged with a solution containing 262 grams of deionized water and 8.0 grams of sodium lauryl sulfate. This mixture is stirred until all of the surfactant is dissolved. The reactor is then placed in a temperature controlled water bath, with continuous stirring, and is brought to 55° C. The solution of monomers and the initiator solution are then fed through syringe pumps into the reactor over a period of 160 minutes with the feed rates remaining constant between 15 to 20 ml/hour. The initiator solution of one feed contained 36 grams of deionized water and 4 grams of ammonium persulfate for all reactions. The other feed contained 36 g distilled water and 4 g sodium bisulfite. The ratio of monomers was varied as shown in Table 3.

TABLE 3

Monomer ratios for emulsion polymerizations.

| Sample ID | Acrylic acid in feed #2 (grams) | MPEGMMA in feed #2 (grams) | Methacrylic acid in feed #2 (grams) |
|---|---|---|---|
| 9501070-28 | 33.80 | 66.48 | |
| 9501070-30 | 16.01 | 32.12 | |
| 9501070-34 | 32.76 | 21.15 | |
| 9501070-35 | 32.78 | 21.01 | |
| 9501070-38 | 18.41 | 35.79 | |
| 9501070-39 | 53.19 | 11.57 | |
| 9501070-41 | | 34.87 | 21.54 |
| 9501070-43 | | 23.19 | 36.16 |

The polymerization for sample 9501070-30, a copolymer of MAA and EG in a ratio of 1:2, contained 21.2 grams of 38% HCl in the reactor charge. This polymerization was a cloudy white dispersion while at 55° C. but became clear and thick when allowed to cool to room temperature. The resulting latex had the following characteristics.

Particle size: 55° C.: approx. 3000 angstroms
24° C.: 1390 to 2160 angstroms

Example 5

This example illustrates the emulsification properties of the complexing graft copolymer emulsifiers described in Example 1.

Emulsification studies were performed in order to evaluate the surfactant behavior of the copolymers at various pH values. Representative oil phases were chosen for these studies. Methyl laurate, dibutyl phthalate and dioctyl phthalate were selected as the oil phases. A general procedure for the emulsification studies is described below while the following table illustrates the different variables studied and the outcome of the tests. Known amounts of copolymer (or PMAA control) (ranging from between 0.1 wt. % to 0.5 wt. %) were dissolved in 100 ml of deionized water with constant stirring for 8–10 hours or until a clear solution was obtained. The pH of the resulting solutions were in the range of 4 to 4.5 for the polymer concentrations studied. About 10 ml of each solution was placed in small glass vials followed by pH adjustment for each vial. The pH was adjusted by adding microliters of either a 1M HCl solution or a 1M NaOH solution. Values of target pH ranged between 1.5 and 13. These solutions of the emulsifier at various pH's were stirred and then 8 ml of each were pipetted out and transferred into stoppered graduated cylinders. To each cylinder, 2 ml of the oil phase was added and the resulting two-phase mixture was well agitated for about 2 minutes and then allowed to stand. The emulsion quality and volume was recorded over time. The emulsions prepared were visually characterized in terms of the following definitions. The oil layer was characterized as clear; hazy, which implies translucence; cloudy or milky, which implies opaqueness; or any combination of the above. The water layer was described as clear; lacy or bubbles present; hazy; cloudy or milky; or any combination of the above. The overall emulsion was described using the following terms: loose and lacy; cloudy or milky; creamy; or any combination of the above. Cloudy emulsions are quite fluid and relatively unstable while creamy emulsions have a thick consistency like mayonnaise and are stable. A bubbly oil phase was interpreted as an unstable emulsion, i.e. 0% oil emulsified, while a creamy emulsion was interpreted as 100% oil emulsified. The emulsification results and comparisons with relevant controls are summarized in Table 4 below:

TABLE 4

Emulsification characteristics of various copolymers as a function of pH.

| Polymer | Solution pH | % Oil Emulsified | Nature of emulsion |
|---|---|---|---|
| 1. 10:1 PMAA-g-PEG1000 | 2.5 | 100 | creamy |
| | 4.5 | 100 | creamy/bubbly |
| | 7.0 | 50 | partially creamy/clear |
| 2. 15:1 PMAA-g-PEG1000 | 2.5 | 100 | creamy |
| | 4.5 | 100 | creamy |
| | 7.0 | 0 | no emulsion |

TABLE 4-continued

Emulsification characteristics of various copolymers as a function of pH.

| Polymer | Solution pH | % Oil Emulsified | Nature of emulsion |
| --- | --- | --- | --- |
| 3. 20:1 PMAA-g-PEG1000 | 1.5 | 100 | creamy |
| | 3.0 | 100 | creamy |
| | 5.0 | 25 | partially creamy |
| | 7.0 | 10 | partially cloudy |
| | 9.0 | 0 | no emulsion |
| 4. inf:1 PMAA (no PEG) | 1.5 | 0 | bubbly oil phase |
| | 3.0 | 0 | bubbly oil phase |
| | 5.1 | 0 | hazy oil phase |
| | 7.0 | 0 | no emulsion |
| | 9.1 | 0 | no emulsion |

All of the above emulsions were observed over time and classified as stable when the emulsion quality did not change over a period of 5 days. In order to test the reversibility of the emulsification process, small quantities of 1M NaOH were added to the emulsions (at low pH) and within a matter of an hour 100% of the oil was released and two clear immiscible phases could be observed thereby confirming reversibility.

Example 6

This example illustrates the thickening properties of the complexing copolymer thickeners described in Example 1.

The viscosities of the polymers of Example 1 were evaluated in the complexed and uncomplexed states and the results tabulated below, showing a large viscosity transition between the complexed and uncomplexed states.

Viscosity studies were performed on a Brookfield viscometer at room temperature on a 0.5 wt. % solution of the 20:1 PMAA-g-PEG1000 copolymer in water at several pH values. The pH was adjusted using small amounts of 1M HCl or 1M NaOH solutions. A large reversible transition in the solution viscosity with pH was observed making this copolymer well suited for use as a thickener.

TABLE 5

Variation of viscosity with pH for a 0.5 wt. % solution of 20:1 PMAA-g-PEG1000 in water.

| pH | RPM | Viscoscity (cP) |
| --- | --- | --- |
| 2.3 | 30 | 1.7 |
| 5.8 | 12 | 29.2 |
| 7.0 | 6 | 107.0 |

Example 7

This example illustrates the synthesis of complexing copolymer beads comprising reversible hydrophobic functionalities synthesized by aqueous free radical suspension polymerizations. Crosslinked copolymers were synthesized using suspension polymerization as outlined below.

Beads of a copolymer of MPEGMMA and AA were formed via suspension polymerization. The procedure for the polymerization consisted of placing 300 grams of deionized water, 0.60 grams of TAMOL-731 (dispersing agent from Rohm & Haas), 3.20 grams of ethylene glycol dimethacrylate (EGDMA) (as crosslinking agent), and 0.133 grams of VAZO-52 initiator in a 500 ml reactor. The reactor was continuously stirred using a magnetic stirrer. To this solution was added a monomer solution consisting of 26.31 grams of MPEGMMA 1000 and 39.08 grams of AA. The reactor was slowly heated to 55° C. for approximately 1 hour and then maintained at that temperature for 5 hours. Initially the solution was cloudy white and then gradually turned to a cloudy yellow color. After about 4.5 hours beads began to drop out of solution and the remaining solution clarified with only a slight yellow tinge remaining. The beads were then isolated and dried for further analysis. The supernatant was neutralized to a pH of about 8 and dried in order to determine its composition.

Example 8

This example illustrates the synthesis of a latex copolymer comprising reversible hydrophobically associating functional groups synthesized by the emulsion polymerization of methacrylic acid, poly(ethylene glycol 400 methacrylate) and comonomer behenyl poly(ethoxy ethyl methacrylate).

The synthesis was conducted in a round bottom reaction flask fitted with a stirrer and using a nitrogen purge. 262.3 g distilled water and 8.02 g of sodium lauryl sulfate surfactant were placed into a round bottomed reaction flask. Feed No. 1 contained 36.02 g distilled water and 4.0 g ammonium persulfate initiator. Feed No. 2 contained 36.0 g distilled water and 1 g sodium bisulfite. Feed No. 3 contained 17.37 g methoxy poly(ethylene glycol) 400 methacrylate (from Polysciences), 36.3 g methacrylic acid, and 6.36 g behenyl polyethoxy ethyl methacrylate.

The reaction was polymerized for 3 hours at 55° C. with agitation. Feed No. 1 was added at a rate of 15 ml/hr, Feed No. 2 at 15 ml/hr and Feed No. 3 at 20 ml/hr. A dilute dispersion of the resulting latex, i.e. 1 part reaction product to 9 parts water, had a viscosity of 2.8 centipoise at a pH of 3 and 2262 centipoise at a pH of 7 (measured at 25 reciprocal seconds shear rate) and an average particle size of approximately 2000 to 3000 angstroms (measured by hydrodynamic chromatography).

Example 9

This example illustrates the synthesis scheme for the preparation of copolymer beads comprising reversible hydrophobic functionalities as described in Example 7 using methacrylic acid in place of acrylic acid.

The following ingredients were reacted based upon the technique described in Example 7.

0.138 g VAZO-52

3.32 g Ethylene glycol dimethacrylate (EGDMA) crosslinker 2.65 g TAMOL 731 dispersing agent (available from Rohm & Haas)

23.43 g methoxy poly(ethylene glycol) methacrylate 1000 (PEGMA 1000)

43.63 g methacrylic acid 351 g water

This reaction was run with stirring for 3 hours at 55° C. The resulting particles were dried in vacuo. Microparticles with diameters of approximately 0.2 mm were obtained.

Example 10

This example illustrates the synthesis of a hydrophilic homopolymer using reversible hydrophobically associating functional groups synthesized by the emulsion polymerization of methacrylic acid or acrylic acid and poly(ethylene glycol).

The procedure for this method is the same as illustrated in example 8 with the exception that the oligo(ethylene glycol) mono-methacrylate is replace by poly(ethylene glycol) of molecular weight 10,000 and the resulting polymer is a homopolymer of methacrylic acid. Hence the presence of the long chain poly(ethylene glycol) permits the emulsion polymerization of a hydrophilic monomer by forming hydrophobic complexes. Similar results can be obtained using poly (ethylene glycol) molecular weights of 2000 or higher.

A dilute dispersion, i.e., 1 part reaction product to 9 parts water, had a viscosity of 3.5 centipoise at a pH of 3 and 171 centipoise at a pH 8.5 (measured at 25 reciprocal seconds shear rate).

The embodiments of the invention in which an exclusive property or privilege is claimed are defined as follows:

1. A graft copolymer comprising a backbone formed primarily from hydrophilic segments comprising Lewis acid repeating units, and grafts which are primarily hydrophilic segments comprising Lewis base repeating units;

wherein the hydrophilic segments comprising Lewis acid repeating units are formed by polymerization of monomers selected from the group consisting of acrylic acid, methacrylic acid, itaconic acid, maleic acid and vinyl phenol;

wherein the hydrophilic segments comprising Lewis base repeating units are formed by polymerization of monomers selected from the group consisting of alkylene oxide, ethylene glycol, vinyl pyrrolidone, and acrylamide;

the hydrophilic segments comprising Lewis acid repeating units including a plurality of acid functional groups, and the hydrophilic segments comprising Lewis base repeating units including a plurality of Lewis base functional groups, the Lewis acid groups and the Lewis base groups being present in a stoichiometric 1:1 molar ratio.

* * * * *

UNITED STATES PATENT AND TRADEMARK OFFICE
CERTIFICATE OF CORRECTION

PATENT NO.   : 5,739,210
DATED        : APRIL 14, 1998
INVENTORS    : ALEC B. SCRANTON, ARVIND M. MATHUR AND JOHN (NMI) KLIER

It is certified that error appears in the above-identified patent and that said Letters Patent is hereby corrected as shown below:

Column 1, line 50;

"Makrotool." should be --Makromol.--.

*Column 13, line 3;

"replace" should be --replaced--.

Signed and Sealed this

Twenty-fifth Day of August, 1998

Attest:

BRUCE LEHMAN

*Attesting Officer*            Commissioner of Patents and Trademarks